United States Patent [19]

Dietz

[11] Patent Number: 4,602,643

[45] Date of Patent: Jul. 29, 1986

[54] PNEUMATIC BREATHING BELT SENSOR WITH MINIMUM SPACE MAINTAINING TAPES

[76] Inventor: Henry G. Dietz, 80 Salisbury Ave., Garden City, N.Y. 11530

[21] Appl. No.: 650,707

[22] Filed: Sep. 14, 1984

[51] Int. Cl.$^4$ .............................................. A61B 5/08
[52] U.S. Cl. ..................................................... 128/721
[58] Field of Search .............. 128/721, 728, 677, 678, 128/30.2, DIG. 15, 687–689, 716, 725, 773, 782

[56] References Cited

U.S. PATENT DOCUMENTS

| | | | |
|---|---|---|---|
| 2,194,809 | 3/1940 | Powell, Jr. | 128/721 |
| 2,233,506 | 3/1941 | Azaretti | 128/721 |
| 3,368,550 | 2/1968 | Glascock | 128/30.2 |
| 3,481,327 | 12/1969 | Drennen | 128/30.2 |
| 4,373,534 | 2/1983 | Watson | 128/721 |

FOREIGN PATENT DOCUMENTS

| | | | |
|---|---|---|---|
| 1480160 | 4/1967 | France | 128/721 |
| 550710 | 7/1956 | Italy | 128/30.2 |

Primary Examiner—William E. Kamm

[57] ABSTRACT

A respiration monitor comprising a sensing unit which senses the expansion and contraction of the chest, abdomen, side or back, by pneumatic means. Expansion of the chest is changed into a positive flow of air (pressure). Contraction of the chest is changed into a negative flow of air (vacuum). The sensor in the form of a belt with minimum space maintaining tapes is worn by the patient and connected to an appropriate monitor by means of tubing. The minimum space maintaining tapes allows the patient freedom of movement and prevents such body movements from affecting the operation of the sensor.

1 Claim, 5 Drawing Figures

PNEUMATIC BREATHING BELT SENSOR WITH MINIMUM SPACE MAINTAINING TAPES

SUMMARY OF THE INVENTION

This invention relates to a respiratory sensor that senses the expansion and contraction of the chest, abdomen, side or back by pneumatic means.

It is an improvement over the device shown in the inventor's pending application "Breathing Sensor", received at Commissioner of Patents and Trademarks Aug. 31, 1984 (Ser. No. 646,294).

This invention is of low cost and requires only tubing to be connected between the sensor on the patient and the monitor.

It is a passive device and incurs no hazards associated with many devices using electrical circuits.

A principal object of this invention is to provide a breathing sensor to detect apnea. Apnea is the cessation of respiratory air flow lasting more than ten seconds. It is a serious problem which becomes dangerous, especially in infants; there exists the possibility of a relationship between prolonged apnea and sudden infant death. In adults it can be the cause of death, and monitoring apnea can help in the diagnosis of upper airway obstructions, congestive heart failure, nervous disorders in the early stages of sleep, etc.

Another principal object of the invention is to make the device so simple that it can be disposable due to its low cost.

Another principal object of the invention is to have a breathing sensor that is extremely confortable for the patient to wear. The invention does not restrict the expansion of the chest. The sensor is in the form of a belt that is fastened by suitable means to fit loosely around the patient's chest when the patient inhales deeply. The fit is not critical since the device is self-adjusting.

Another principal object of the invention is to have a single adjustable device so that one size will fit patients of unlike chest expansion.

Another principal object of the invention is that movement of the patient, such as turning in bed, will result in the device readjusting to the new condition, and that it be capable of sensing the respiration without any need of the device being reapplied.

Another principal object of the invention is that it can be easily manufactured with a minimum of parts made from low cost materials.

Still another object of the invention is that it can be made to fit babies, children, and adults with ease.

Other objects, uses and advantages, will be obvious, or become apparent from a consideration of the following detailed description and the application drawings.

However, it is to be distinctly understood that the specific drawing illustrations provided are supplied primarily to comply with the requirements of the patent laws, and that the invention may have other embodiments which will be obvious to those skilled in the art, and which are intended to be covered by the appended claims.

DESCRIPTION OF THE PREFERRED EMBODIMENTS

Figure 3:
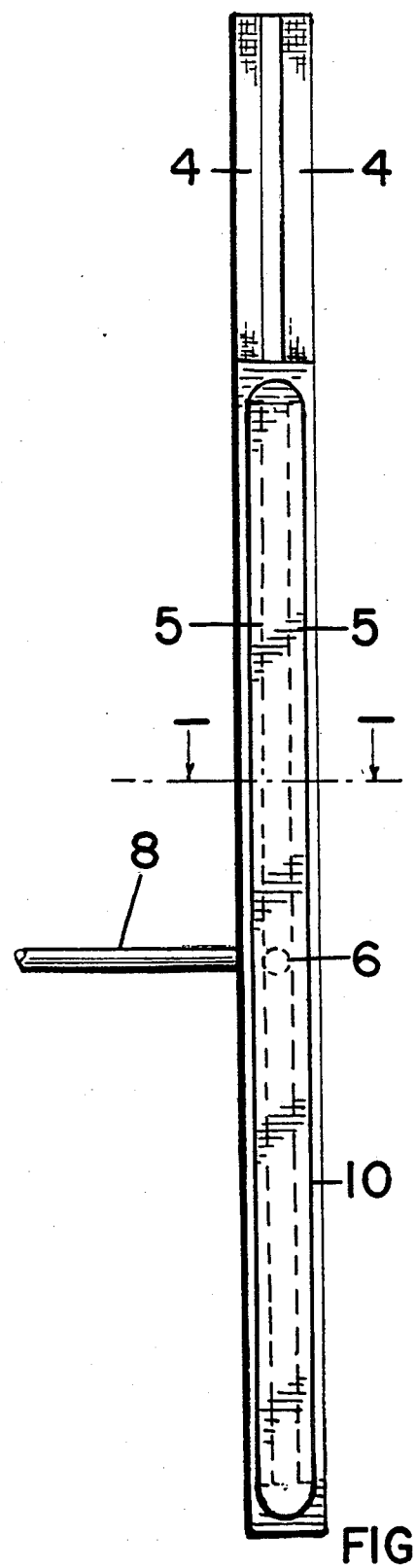
FIG. 3 is a front elevation view of the sensor.
Figure 4:
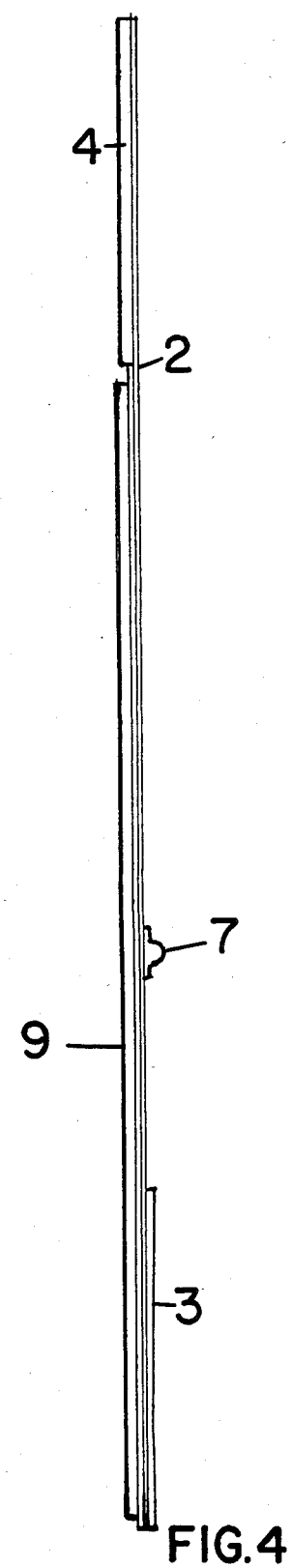
FIG. 4 is a side elevation view of the sensor.
Figure 5:
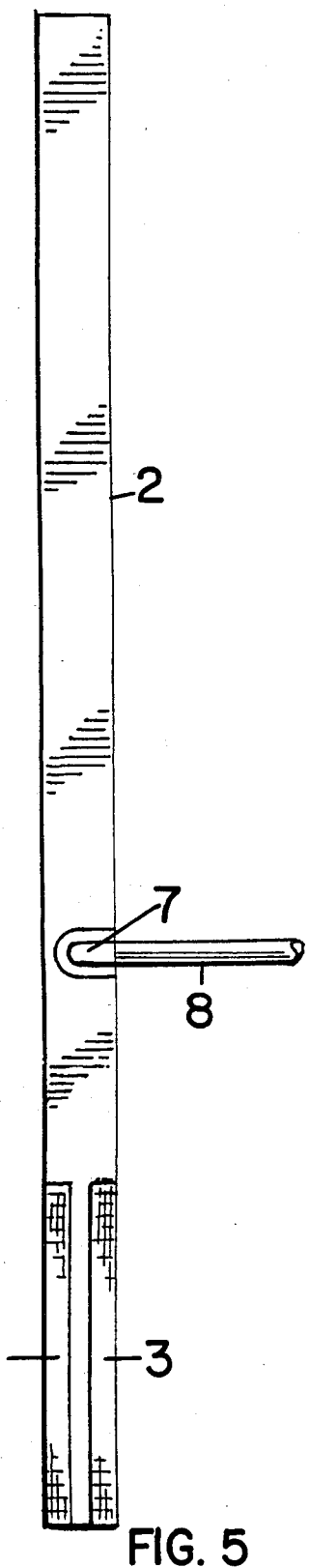
FIG. 5 is a rear elevation view of the sensor.

FIGS. 1, 2, 3, 4, and 5 generally indicates a preferred embodiment of the invention which comprises an essentially rectangular shaped belt 2 FIG. 5 of flexible material made from sheet vinyl plastic or other suitable material having equivalent characteristics.

The belt 2 of flexible material is provided with a means of fastening the two ends together and means for adjusting the size to meet the requirements of the patient. FIGS. 3, 4, and 5 show a preferred embodiment where Velcro (trademark Velcro U.S.A. Inc.) tape fastener is used for this purpose. Velcro is a woven and molded hook and loop fastener. The woven and molded hook 3 consists of 2 tapes fastened to belt 2 with adhesive or other suitable means of fastening at the extremity of one end of the belt 2. The extremity of the other end of the belt 2 on the opposite side is provided with two tapes of woven and molded loops 4 fastened to the belt 2 with adhesive or other suitable means of fastening.

Figure 2:
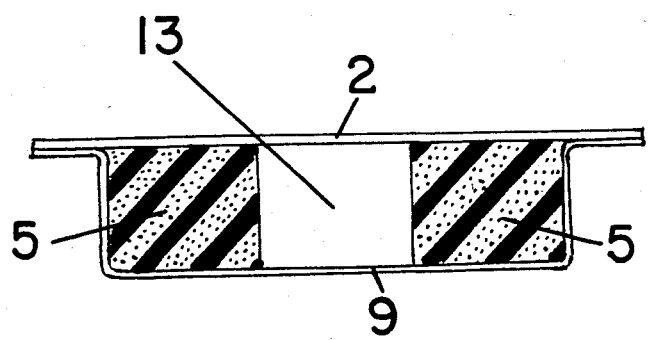
FIG. 2 is a sectional view taken substantially along line 1—1 of FIG. 3.

A suitable elastic reaction in the form of a tape 5, essentially rectangular in cross section made of a foam material, sponge rubber or other suitable material is fastened with adhesive to belt 2 as shown in FIG. 2. The two tapes 5 are assembled by aligning on the belt 2 longitudinally as indicated by the dotted outline on FIG. 3. A vent hole 6 is provided in the belt 2 communicating with a molded plastic street elbow 7 fastened to belt 2 with adhesive or other suitable means of fastening to provide means for connecting a suitable flexible tube 8. Flexible tube 8 communicates with the vent hole 6. A very thin sheeting 9 is assembled over the tapes 5. The sheeting 9 can be a very thin sheet of vinyl or other suitable material. A preferred way of manufacturing would be to have a rule type die made in a rectangular shape with round ends as shown by line outline 10.

This die would be used with a high frequency or ultrasonic machine to make a heat seal between belt 2 and the thin sheeting 9 following the unbroken circumambient relation of line outline 10 to effect a good fluid tight seal between belt 2 and the thin sheeting 9. Sealing could also be accomplished with adhesive and the invention is not to be limited to the heat or sonic sealing described.

Figure 1:
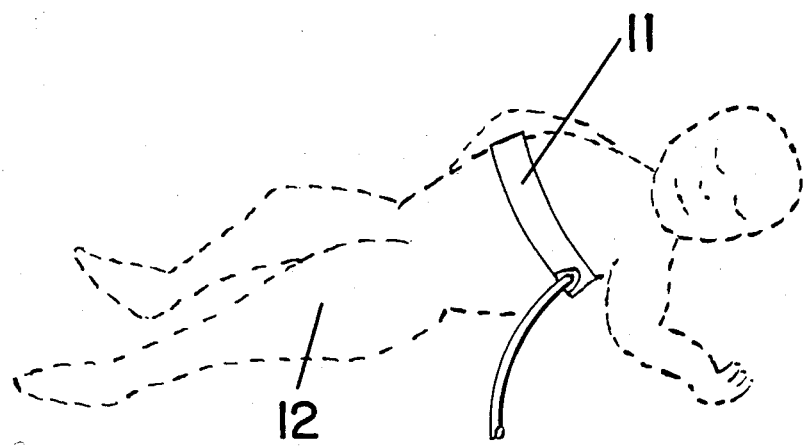
FIG. 1 is a perspective view of an infant with the sensor belt worn around the chest.

The assembly described is the Pneumatic Breathing Sensor 11 around the chest of an infant 12 or adult as in FIG. 1 with the thin sheeting 9 adjacent to the skin.

The Pneumatic Breathing Sensor 11 is fitted loosely around the chest so that the elastic reaction tapes 5 are compressed when the chest is fully expanded as in deep inhaling. Exhaling results in the chest contracting and tapes 5 are then fully expanded. The air space 13 between tapes 5 is of largest volume when respiration air is being exhaled, and smallest volume when respiration is being inhaled. The action of inhaling and exhaling results in a flow of air in tube 8, such that inhaling produces a positive flow (pressure) and exhaling produces a negative flow (vacuum).

When tube 8 is connected to a breathing sensor as described in the pending patent application "Breathing Sensor", the respiration is changed to an electrical signal. The patent pending breathing sensor is a sensor consisting of a tubular passage having a loosely fitting ball that interrupts a light source to indicate breathing.

The patient can turn over in the bed, when this happens, part of the tapes 5 is compressed by the weight of the body. The increased pressure obtained from the reduction of the air space 13 escapes through the loose fit of the ball in the tubular passage of the breathing sensor. The air space 13 is never completely closed since tapes 5 always have some height when fully compressed and air can always reach the vent 6. Shortly after the patient has turned over in bed, air is being bled off and the pneumatic breathing sensor 11 functions to indicate inhalation and exhalation of the patient.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. A pneumatic breathing sensor for use on the chest of a patient, including an infant, comprising:
    an essentially rectangular belt of compliant material having means for fastening the ends of said belt around the chest of the person
    a casing of compliant material extending along the exterior of the belt and sealed thereto forming an enclosed air space, a tube sealed to the casing and in communication with the air space for conveying pressure changes in the air space due to the person's breathing to a utilization device and
    means for elastically maintaining a reduced passageway in the air space in communication with the tube under the weight of the person, including two longitudinally extending and laterally spaced tapes of resilient material secured to the belt inside the casing.

* * * * *